US 6,837,895 B2

(12) United States Patent
Mayenberger

(10) Patent No.: US 6,837,895 B2
(45) Date of Patent: Jan. 4, 2005

(54) INSTRUMENT FOR PLACING SURGICAL CLIPS

(75) Inventor: Rupert Mayenberger, Rielasingen (DE)

(73) Assignee: Aesculap AG & Co. KG, Tuttlingen (DE)

( * ) Notice: Subject to any disclaimer, the term of this patent is extended or adjusted under 35 U.S.C. 154(b) by 406 days.

(21) Appl. No.: 10/051,625

(22) Filed: Jan. 18, 2002

(65) Prior Publication Data

US 2002/0099388 A1 Jul. 25, 2002

Related U.S. Application Data

(63) Continuation of application No. PCT/EP00/07010, filed on Jul. 21, 2000.

(30) Foreign Application Priority Data

Jul. 23, 1999  (DE) .......................................... 199 34 634

(51) Int. Cl.⁷ .............................................. A61B 17/10
(52) U.S. Cl. ...................................... 606/142; 606/143
(58) Field of Search ................................ 606/142, 143; 227/175.1

(56) References Cited

U.S. PATENT DOCUMENTS

| 4,430,997 A | 2/1984 | DiGiovanni et al. |
| 4,512,345 A | 4/1985 | Green |
| 5,843,097 A | * 12/1998 | Mayenberger et al. ...... 606/143 |
| 6,352,541 B1 | 3/2002 | Kienzle et al. |

FOREIGN PATENT DOCUMENTS

| DE | 196 03 889 | 8/1997 |
| WO | 99/27859 | 6/1999 |

* cited by examiner

*Primary Examiner*—Julian W. Woo
(74) *Attorney, Agent, or Firm*—Barry R. Lipsitz; Douglas M. McAllister

(57) ABSTRACT

An instrument for placing U-shaped surgical clips comprising a magazine that has a distal and a proximal end in which several clips are arranged one behind the other in a guide that can be pushed in longitudinal direction. On the lower side of the magazine, a feeding plate which by means of flexible lugs is in contact with the back sides of the clips and can be pushed forwards and backwards by means of a pushing device over at least a distance between one clip and the next clip parallel to the guide of the magazine is provided. The movement of pushing forward shifts all the clips in the direction of the distal end of the magazine. When the feeding plate is pushed forwards, the pushing device contacts said feeding plate at a point which is at a distance of at least half a length of the feeding plate away from the proximal end of the feeding plate.

17 Claims, 5 Drawing Sheets

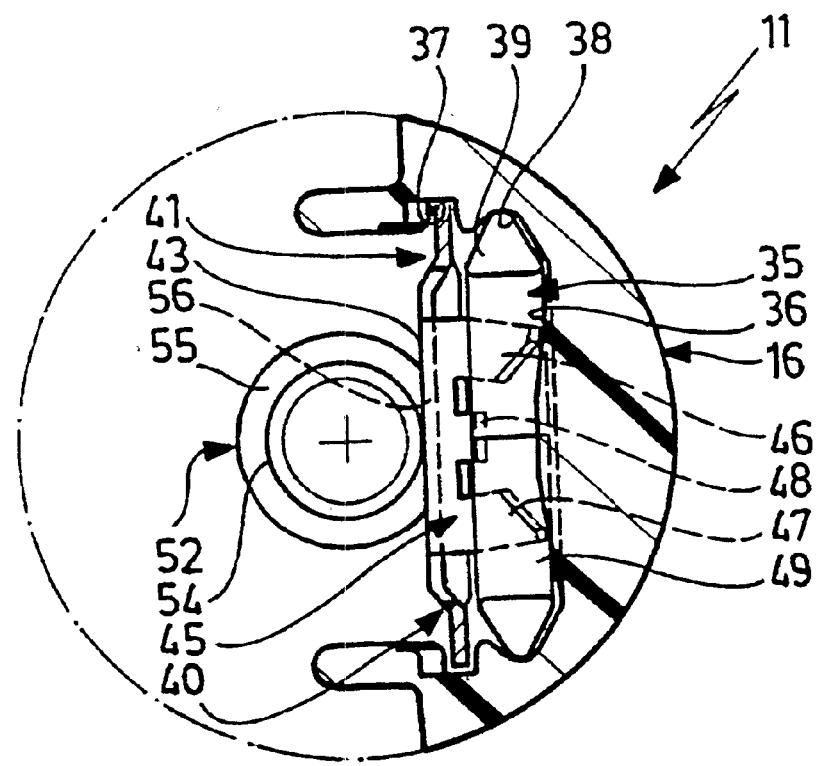
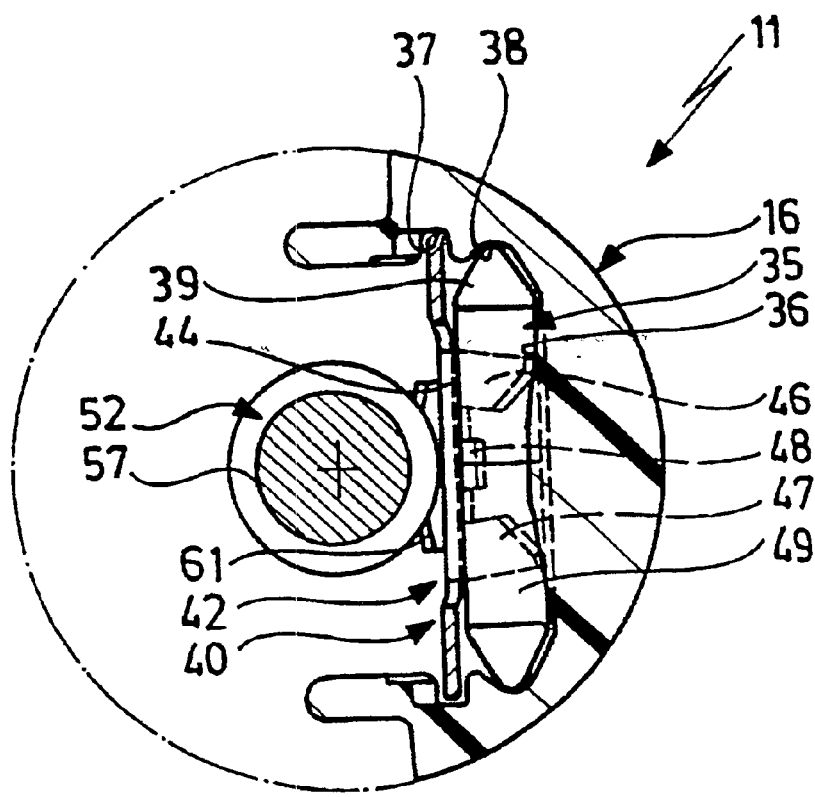

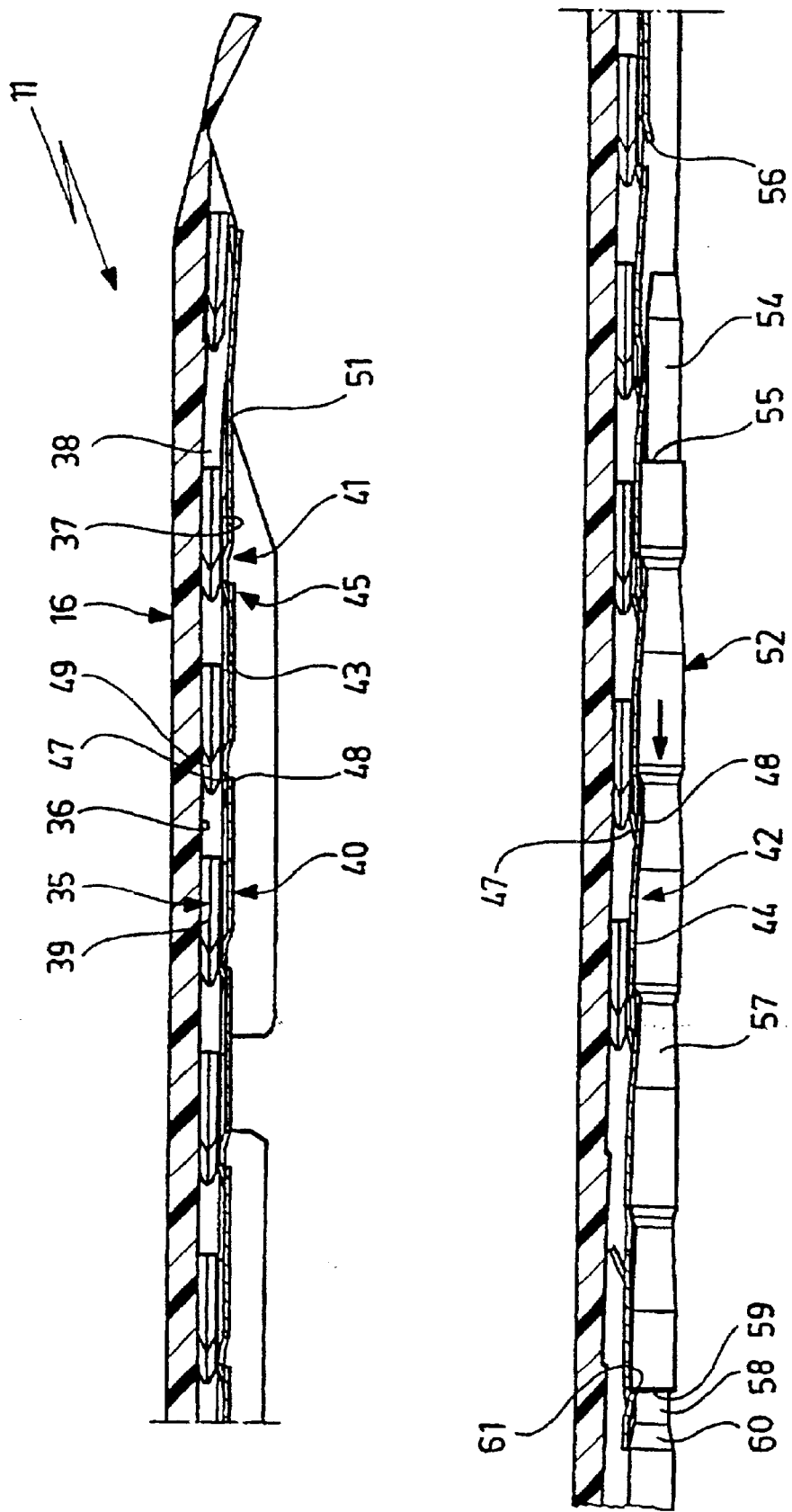

INSTRUMENT FOR PLACING SURGICAL CLIPS

The present disclosure relates to the subject matter disclosed in the international application No. PCT/EP00/07010 of Jul. 21, 2000, which is incorporated herein by reference in its entirety and for all purposes.

BACKGROUND OF THE INVENTION

The invention relates to an instrument for placing U-shaped surgical clips comprising a magazine that has a distal end and a proximal end and in which several clips are arranged one behind the other in a guide and can be moved in the longitudinal direction. On the lower side of the magazine, a feeding plate is provided which contacts the back side of the clips by means of flexible lugs and which can be pushed forwards and backwards parallel to the guide of the magazine over at least the distance between two clips by means of a pushing device. The pushing device creates a pushing movement which shifts all the clips in the direction of the distal end of the magazine.

A placing instrument of this kind is for example known from DE 196 03 889 A1. In the case of this known placing instrument a pushing device shaped like a bar engages on a feeding plate at its proximal end and pushes said plate forwards during the pushing movement and pulls it back again. During the pushing movement the feeding plate must transmit pushing force to all clips arranged in the magazine so that the clips are pushed forward one position at a time during this pushing movement.

In the case of customary placing instruments this is of course possible. However, great difficulties arise when the placing instrument is to be made smaller, especially when the outside diameter of the instrument is to be reduced. When this diameter is reduced the components arranged in the shaft must also be reduced in their measurements, and in doing so problems with the stability of the different parts can result.

The object of the invention is to construct a placing instrument of the kind in the preamble in such a way that the large amount of force necessary to push the clips forward can be provided without difficulty when the measurements of the instrument are reduced.

SUMMARY OF THE INVENTION

In the case of a placing instrument as described at the outset this object is achieved in accordance with the invention in that the pushing device of the feeding plate when pushed forwards acts on a point that is at least half a length of the feeding plate away from the proximal end of the feeding plate.

This construction prevents the feeding plate from being pushed forwards from the proximal end during the pushing movement. In the new construction in which the pushing device acts on a point on the feeding plate which is offset on the feeding plate at least half a length, half of the feeding plate at the most is pushed during the movement of pushing forwards, while the other half of the feeding plate is pulled. When the point of action is set even further in the distal direction, this relation is changed even further, such that the region of the feeding plate that is pulled then becomes even larger. During the forward movement the pulling forces are more advantageous for the feeding plate because breakage of the feeding plate when exposed to pushing forces is prevented. During the movement of pushing the feeding plate forwards the force is much larger than during the movement of pulling it back because during the movement of pushing forwards the clips in the magazine must be pushed forwards also, while during the movement of pulling back only the empty feeding plate is drawn past the clips that have been pushed forwards.

By this embodiment it is possible to also use feeding plates which consist of very thin materials and therefore are not strong enough to prevent breaking away when used in known placing instruments, even if beads have been indented.

The stability of this feeding plate can furthermore be increased by providing the feeding plate with a middle section that stands out downwards in the region arranged distally to the point of action of the pushing device and that runs at a distance from the clips transported in the magazine. This middle section standing out downwards forms a stiffened bead which reinforces this region of the feeding plate against undesirable breaking out, so that in this region occupying half the length of the feeding plate at the utmost a relatively large pushing force can be transmitted.

Furthermore it can be provided for the feeding plate to have a middle section in its region arranged proximally to the point of action of the pushing device which stands out upwards and which runs along close to the clips transported in the magazine. This middle section standing out upwards can also be formed like a kind of bead and serves to stiffen the feeding plate. In addition a chamber hereby results in the proximal region of the feeding plate and below it to receive the pushing device so that the size of the construction of the placing instrument can be reduced in total. It is also advantageous in this respect that additional stiffening can be achieved through the different direction of the beads in the distal region and in the proximal region of the feeding plate.

In accordance with a particularly preferred embodiment it is provided for the pushing device to be a bar that is arranged under the feeding plate and that can be pushed forwards and backwards. When pushed forwards the bar contacts a side projection of an edge of the feeding plate which stands out downwards from the plane of the feeding plate.

It is preferable for this edge to be formed by the middle section of the feeding plate standing out downwards. In contrast to the known placing instruments it is this way no longer necessary to set the pushing device close to a flexible tongue of the feeding plate facing downwards which could be undesirably deformed under high strain. Instead, the force is transmitted by the middle section of the feeding plate standing out downwards so that the pushing device does not exert a turning moment onto a part connected to the feeding plate but rather can transmit the pushing force directly in the pushing direction into the feeding plate.

In another preferred embodiment it is provided for the bar to be arranged proximally to the side projection close to the middle section of the feeding plate and to have recesses which form chambers to receive the flexible lugs of the feeding plate when the bar is pushed back.

An embodiment of this kind on the one hand makes it possible to arrange the feeding plate very close to the clips in the proximal region and in addition to use the space directly below the feeding plate for the pushing device. Despite this very compact arrangement the flexible lugs lying close to the clips can glide past the bottom of the clips when the feeding plate is pulled back, because they can plunge into the vacant chambers of the pushing device and therefore have enough space to evade the passing clips. All in all a particularly compact arrangement is achieved this way.

It is advantageous when the bar has a circular cross-section and when the side projection and the recesses are formed as ring collars or ring grooves respectively that run around the bar. In such an embodiment the edge of the middle section of the feeding plate that stands out downwards plunges into the cross section of the circular bar in the distal region so that the bar can direct the pushing force on the front side directly into the feeding plate. Even if the feeding plate is made very thin this results in the force being transmitted safely without the danger of said feeding plate breaking away to the sides.

It can also be provided that when the pushing device is pushed back a side projection lies close to a flexible lug of the feeding plate, the flexible lug preferably being arranged at the proximal end of the feeding plate, which means that the feeding plate is pulled when pushed back.

In this respect it is advantageous when the side projections of the pushing device are less far away from each other than the corresponding points of action on the feeding plate. Thereby it is possible to provide the pushing device with a reciprocal movement that is larger than the space between the clips arranged in the magazine. Nevertheless the feeding plate is pushed forwards and backwards only as far as the space between two clips at a time. This is particularly advantageous when different handles for the placing instrument are to be used to operate the pushing device which produce different pushing movements of the pushing device in accordance with their type of construction.

In principle the feeding plate can be part of the placing instrument, but it is particularly advantageous for the feeding plate to be in the magazine movable in longitudinal direction parallel to the guide of the clips, which means that it is part of the magazine. When the magazine is inserted, preferably into a shaft on the side of the placing instrument, the magazine may be positioned in a way that the side projections act on the feeding plate between the corresponding points of action so that the feeding plate is inevitably carried along when the pushing device is pushed forwards and pulled back.

In the guide of the magazine the clips can preferably be held in a detachable clasp or frictional connection so that the clips are transported by the feeding plate during the movement of pushing it forwards as far as the distance between two clips. The clips stay in this position when the feeding plate is pulled back and the flexible lugs situated close to the clips move alongside the clips elastically and snap back to their receptive position behind each clip.

The following description of preferred embodiments of the invention serves to explain it further in connection with the attached drawings.

BRIEF DESCRIPTION OF THE DRAWINGS

FIG. 4: shows a sectional view taken along the lines 4—4 in FIG. 3;

FIG. 5: shows a sectional view taken along the lines 5—5 in FIG. 3; and

FIG. 6: shows a view similar to FIG. 3 during the movement of pulling the feeding plate backwards in proximal direction.

DETAILED DESCRIPTION OF THE INVENTION

Figure 1:
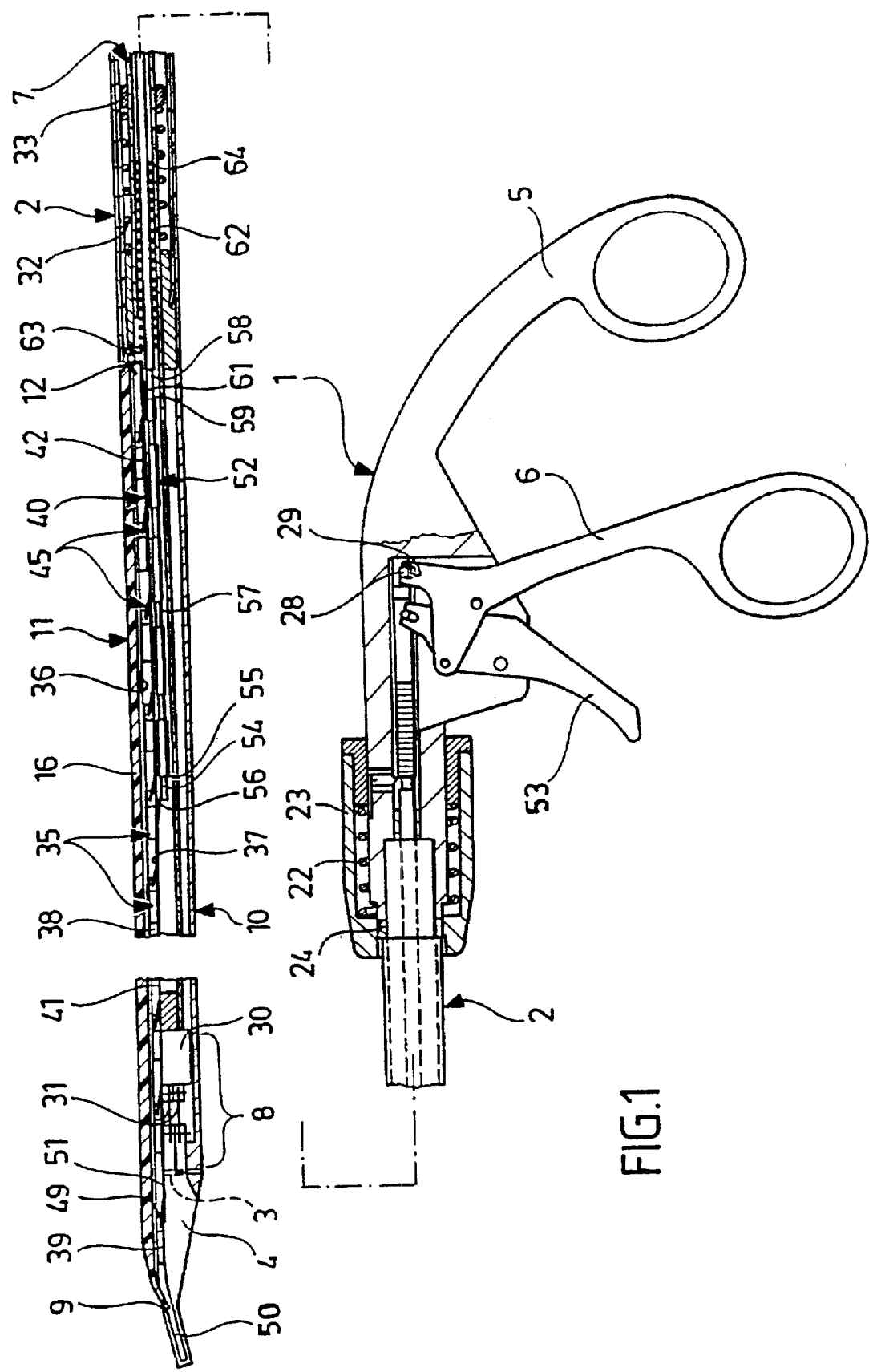
FIG. 1: shows a view in longitudinal section of a placing instrument for surgical clips.

The placing instrument shown in the drawings comprises a handle 1 and a shaft pipe 2 attached to said handle in a way that it is pivotable around its longitudinal axis and detachable. The outside diameter of said shaft pipe is small in comparison with its length. For example the shaft pipe can be 25 cm long, the outside diameter 10 mm or less. At the free end of the shaft pipe 2 two jaws 4 of a plier-like placing tool are arranged that are pivotable around their common swivelling axis 3 and that can be opened and closed from the handle 1 through a locking mechanism arranged in the interior of the shaft pipe. For this purpose the handle 1 is rigidly connected to the first ring handle 5 opposite which a second ring handle 6 is pivotably attached to the handle 1. This second ring handle is pivotably connected to a push-and-pull bar in the form of a sleeve 7 that runs through the whole shaft pipe 2 up to the locking mechanism 8. By pivoting the ring handles 5 and 6 towards each other the jaws 4 of the placing tool can thus be opened and closed as is known for shaft pipe instruments.

Directly adjacent the placing tool formed by the jaws 4 the shaft pipe 2 has an opening 9 that extends along the front part of the pipe shaft and over about 180° in the direction of the circumference so that in the region of this opening 9 the shaft pipe 2 is closed by a lower tray 10 only in the lower half of the shaft pipe but is open on the upper side.

The opening 9 on the upper side of the shaft pipe 2 can be closed by a clip magazine 11 inserted into said opening 9 which basically has a cross section that is nearly semi-circular and which completes the cross section of the shaft pipe 2 to a full circle. Said clip magazine 11 has a projection 12 on its proximal side near the handle which plunges slightly into the shaft pipe 2 at a point directly adjacent to the opening 9 and thereby engages under the edge bordering the opening 9. At the front end two side lobes 13 are integrally formed on the sides which engage into corresponding recesses of the lower tray 10 and which, when joined together, snap with their end sections standing out to the inside into corresponding grooves of the lower tray 10 that are not shown in the drawings, resulting in a flexible clasping of the lobes 13 to the side walls of the lower tray 10 in this region. By the insertion of the projection 12 into the shaft pipe 2 and by this clasp or frictional connection the clip magazine 11 is fixed to the shaft pipe 2 in a stable manner. The connection between the clip magazine 11 and the lower tray 10 can be opened by vigorously pulling off the clip magazine from the lower tray 10.

The shaft pipe 2 plunges into a handle sleeve 23 which can be pushed along the handle 1 in the longitudinal direction against the action of a spring 22. The handle sleeve is part of a click and ratchet locking means that connects the shaft pipe 2 with the handle 1. Said handle sleeve 23, which is arranged on the handle 1 and can be pushed in longitudinal direction, locks several locking elements 24 in a radial interior position when the spring 22 is relaxed. The locking elements 24 are sphere-shaped and can be pushed into radial openings in the handle 1. However, said handle sleeve enables the locking element 24 to move radially outwards when the handle sleeve 23 is pulled back against the action of the spring 22. When they have been pushed in in a radial direction the locking elements 24 plunge into radial recesses of the shaft pipe and lock it in the direction of the axis on the handle, but when pushed out in the radial direction the locking elements 24 release the shaft pipe 2 so that it can be pulled out of the handle 1 in the direction of the axis.

The sleeve 7 arranged in the shaft pipe 2 passes through the connecting point between the shaft pipe 2 and the handle 1 up to the handle and there it is pivotably connected to the ring handle 6 by means of two side cogs 28 which engage into side openings 29. When the ring handle 6 is pivoted relatively to the ring handle 5 the sleeve 7 is thereby pushed forwards into a distal position and backwards into a proximal position.

Figure 2:
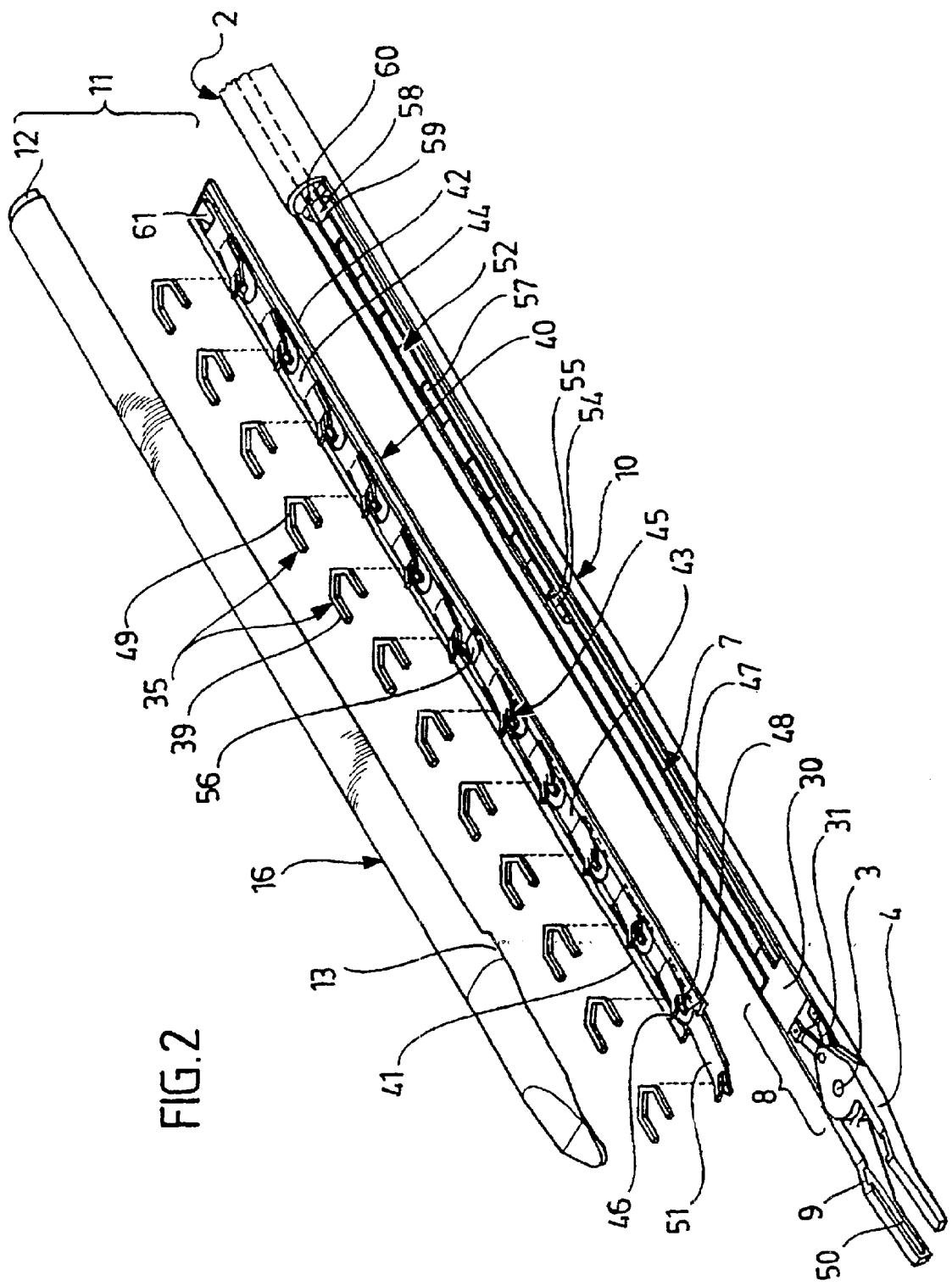
FIG. 2: shows a perspective exploded view of the shaft section of the instrument of FIG. 1.
Figure 3:
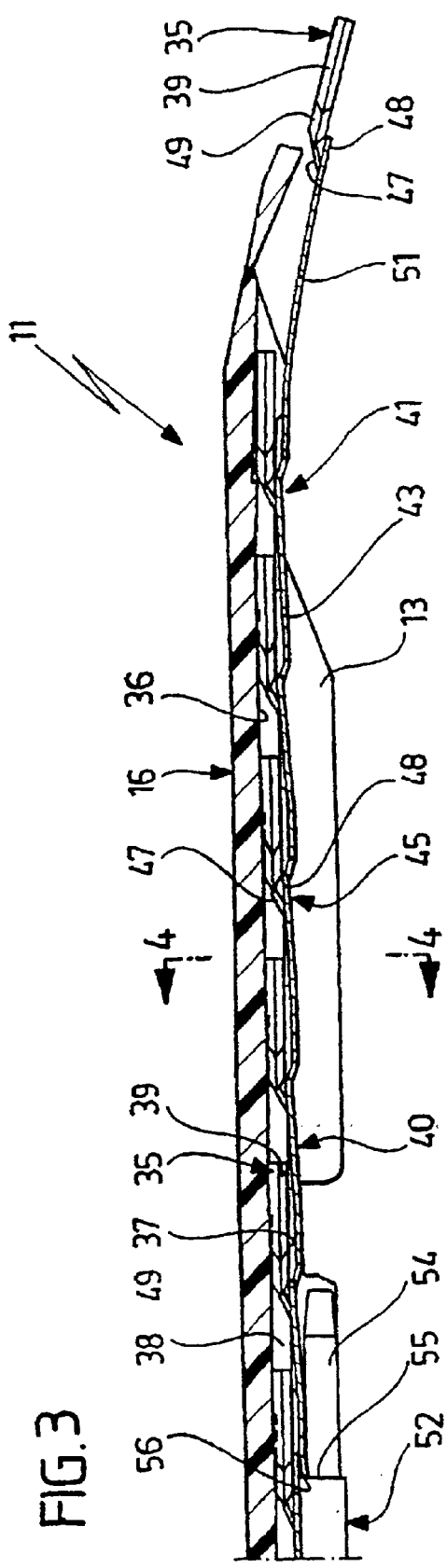
FIG. 3: shows a view in longitudinal section of the magazine and of the feeding plate arranged below the magazine during the movement of pushing the feeding plate forwards in distal direction.
Figure 3:
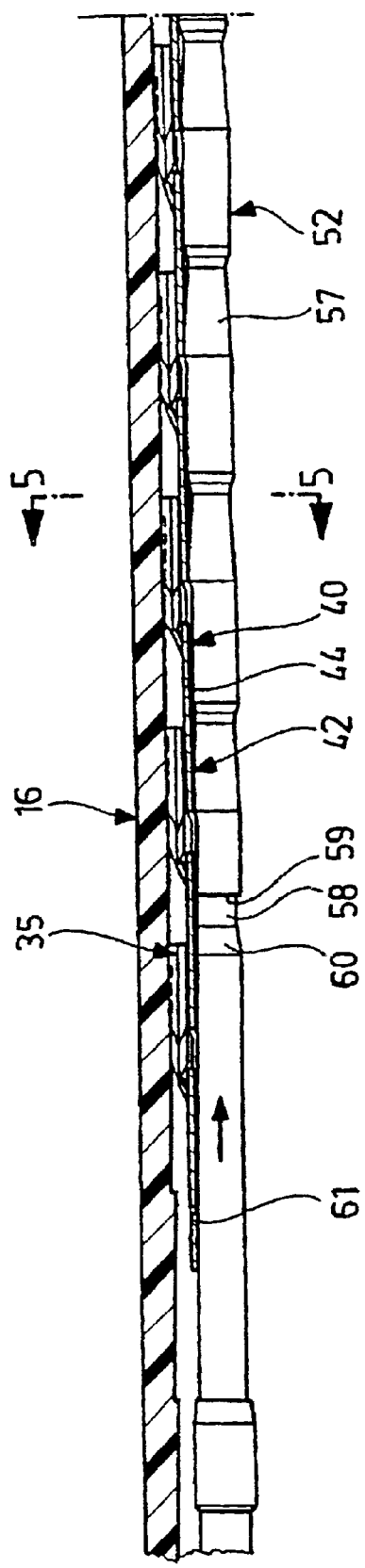

Said sleeve is cut open towards the top in the region of the opening 9 of the shaft pipe 2 so that in this region it forms only a lower tray, the free end of which is firmly connected to a sliding block 30 that is arranged in the lower tray 10. The sliding block 30 fills out the cross section of the tray fully and can be moved in the longitudinal direction. This sliding block 30 is pivotably connected to a jaw 4 of the placing instrument through an individual connecting lever 31 so that each jaw 4 and each connecting lever 31 constitute a knee joint (FIG. 2). This knee joint can be bent more or less when the sliding block 30 is pushed forwards and backwards which leads to a pivoting of the jaws 4. Pulling back the sliding block 30 causes the jaws 4 to open again. This opening is also promoted by a coil spring 32 which coaxially surrounds the sleeve 7 and is supported at the one end by a projection of the lower tray 10 and at the other end by a ring collar 33 which is permanently connected to the sleeve 7. In this manner a spring force in the direction of the handle 1 acts on the sleeve 7 which promotes the opening of the jaws 4.

The whole of the locking mechanism 8, which comprises the sliding block 30, the connecting lever 31 and the back part of the jaws 4, is placed in the lower tray 10. Such an arrangement leaves the whole opening 9 free to take up a mechanism for pushing forwards the clips 35 and to take up the clip magazine 11 in which the clips 35 are situated.

In the clip magazine 11 a receptive chamber 36 for the clips 35 is arranged which is open towards the bottom and has the form of a longitudinal groove in the clip magazine 11. Guiding grooves 38 situated opposite one another are indented in the side walls of this receptive chamber 36 into which the legs 39 of the U-shaped clips 35 plunge. Several of these U-shaped clips 35 are set in a row one behind the other in this way in the receptive chamber 36, thereby staying at a distance in relation to one another (FIG. 2).

Another guiding groove 37 runs parallel to the guiding grooves 38 in each of the side walls. In these grooves 37 a flat feeding plate 40 is supported that runs along the whole length of the clip magazine 11 and can be pushed forwards in the longitudinal direction, the feeding plate thus closing the receptive chamber 36 towards the bottom. Said feeding plate 40 has a distal region 41 adjacent to the jaws 4 and a proximal region 42 facing the handle 1 which are approximately of same length in the described embodiments, each therefore running along half the total length of the feeding plate 40.

In the distal region 41 the middle section 43 of the feeding plate 40 is shaped downwards in the manner of a reinforcing bead so that the plane created by the flat middle section 43 is offset to the plane created by the guiding grooves 37 (FIG. 4). In the proximal region 42 however the corresponding middle section 44 is shaped upwards, in the direction of the clips 35, so that the flat middle section 44 is offset upwards to the plane of the guiding grooves 37 (FIG. 5). In this way the proximal middle section 44 is situated directly adjacent to the lower sides of the clips 35, the distal middle section 43 however remains at a distance from the lower side of the clips 35.

In the distal middle section 43 as well as in the proximal middle section 44 several flexible lugs 45 are formed through longitudinal cuts which through longitudinal cuts each are at their front end divided into three flexible tongues 46, 47, 48 arranged next to one another. The two outer flexible tongues 46, 48 are bent diagonally towards the receptive chamber 36 in the section of their free end so that the free edges run diagonally to the surface of the feeding plate 40 and stand out upwards above said surface in the direction of the receptive chamber 36.

When the feeding plate 40 is in its pulled back in a proximal position these edges are adjacent to the bridge 49 connecting the two legs 39 of a clip 35, the edges thereby running diagonally ensuring that the adjacent position is firm and that the edges are prevented from slipping off even when the contour of the bridge 49 is line-shaped. The middle flexible tongue 47 of the flexible lug 45 contacts the lower side of the clips 35 so that in this way the edges are also safely prevented from slipping over the upper side of the clips 35.

When the feeding plate 40 is pushed in the distal direction each pair of flexible tongues 46, 48 takes along a clip 35 and pushes it one step in the clip magazine in distal direction. Said step corresponds to the distance of the stroke of the feeding plate 40.

The front clip 35 is thereby pushed forward and out of the guiding grooves 38 in the side walls of the receptive chamber 36 and arrives in guiding grooves 50 on the inner sides of the jaws 4, said guiding grooves 50 adjoining the guiding grooves 38 and running in the same direction.

At its front end the feeding plate ends in a flexible lug 51 which is as a whole narrower than the feeding plate 40. When the feeding plate 40 is pushed forwards this flexible lug 51 enters between the jaws 4 and pushes the front clip 35 into the slightly downwards-slanting guiding grooves 50 of the jaws 4 to their front end. Due to the narrow flexible form of the flexible lug 51 in its front part it can follow the slightly modified slant of the guiding grooves 50 easily.

The clip magazine 11 basically consists of a lid-like upper half-shell or upper tray 16 into which the clips 35 and the feeding plate 40 have been inserted in the described way. In FIG. 2 these parts are shown separately for reasons of a better overview.

When the feeding plate 40 is moved backwards the flexible lugs 45 glide alongside the following clips 35 until said lugs all stand behind said clips again and can spring up again into the receptive position in which the edges contact the bridges 49 of the clips 35. Merely by this movement forwards and backwards of the feeding plate 40 one clip is pushed in between the jaws 4 at a time which then can be placed by closing the jaws in the described way, for example to close a blood vessel. This is done until the clip magazine 11 is empty, then a new clip magazine can be inserted in an easy way to replace the one that has been emptied and the operation can continue.

The feeding plate 40 is pushed by a push-and-pull bar 52 which is situated in the interior of the sleeve 7 and can be pushed in the longitudinal direction, and which is pivotably connected to the handle 1 by a swivel lever 53. The tilting movement of said swivel lever shifts the push-and-pull bar 52 in the interior of the shaft pipe and the sleeve 7.

The push-and-pull bar 52 has a circular cross section and runs along the whole of the proximal region 42 below the proximal middle section 44 of the feeding plate 40. With its outside diameter the push-and-pull bar 52 thereby closely contacts the proximal middle section 44.

At its free end the push-and-pull bar 52 has a short section 54 with a smaller outside diameter. Thereby a step 55 running around the bar 52 is formed between the section 54 and the remaining part of the push-and-pull bar 52. Said step 55 comes into contact with an edge 56 of the distal middle section 43 when the push-and-pull bar is pushed in distal direction. Said edge is formed in the transitional region between the distal middle section 43 and the proximal middle section 44 which stand out in opposite directions of the plane created by the guiding grooves 37.

In proximal direction next to the step 55 several ring grooves 57 follow that run around the push-and-pull bar 52. The distance between each of these ring grooves is the same as the distance between the clips 35 in the clip magazine 11. Said ring grooves 57 form receptive chambers for the flexible lugs 45 into which these can enter as they glide along the lower side of the clips 35 and are thereby bent downwards when the feeding plate 40 is pulled back into proximal position.

In the region of the proximal end of the clip magazine 11 another ring groove 58 is inserted in the push-and-pull bar 52 following the ring grooves 57. Said ring groove 58 forms a ring step 59 at its distal end and a glide surface 60 at its proximal end. When the feeding plate 40 is pulled back into the proximal position a flexible lug 61 snaps downwards into this ring groove 58 at the proximal end of the proximal middle section 44 and its free edge comes into contact with the ring step 59 so that the push-and-pull bar 52 takes along the feeding plate 40 in proximal direction when pushed in proximal direction. By pushing the push-and-pull bar 52 forwards and pulling it backwards the feeding plate 40 is thereby also pushed forwards and pulled backwards every time. When pushed forwards in distal direction the force is transmitted through the step 55 coming into contact with the edge 56, when pulled backwards in proximal direction however through the flexible lug 61 coming into contact with the ring step 59.

The distance between the edge 56 on the one side and the flexible lug 61 on the other is chosen larger than the distance between the step 55 and the ring step 59 so that the push-and-pull bar 52 can make a larger movement forwards and backwards and nevertheless shift the feeding plate 40 no more than the distance between two clips in both directions in the magazine. In this way it is possible to adapt to different pushing movements of different handles.

The co-operating connection between the push-and-pull bar 52 on the one hand and the feeding plate 40 on the other is detachable because it is solely produced by the push-and-pull bar 52 being directly adjacent to the feeding bar 40. This connection is formed automatically when a clip magazine 11 is inserted into the shaft pipe 2, it is loosened when the clip magazine 11 is taken out of the shaft pipe 2.

The push-and-pull bar 52 is concentrically surrounded by a coil spring 62 that is supported by a projection 63 of the shaft pipe 2 on the one hand and by a step 64 of the push-and-pull bar 52 on the other hand, thereby shifting these in the proximal pull-back position. The feeding plate 40 is in this way pushed in distal direction against the action of the coil spring 62 which is to be mentioned as situated in the interior of the sleeve 7.

What is claimed is:

1. An instrument for placing U-shaped surgical clips comprising:
    a magazine that has a distal and a proximal end in which several clips are arranged one behind the other in a guide and that can be pushed in a longitudinal direction, and, on the lower side of the magazine, a feeding plate which by means of flexible lugs is in contact with back sides of the clips and can be pushed forwards and backwards by means of a pushing device over at least a distance between one clip and a next clip parallel to the a guiding groove of the magazine, wherein
    the movement of pushing forwards shifts all the clips in the direction of the distal end of the magazine, the pushing device when pushed forwards thereby contacting the feeding plate at a point which is at a distance of at least half a length of the feeding plate away from the proximal end of the feeding plate,
    the feeding plate in its region that is arranged distally to the contact point of the pushing device has a middle section standing out downwards which runs along at a distance to the clips guided in the magazine, and
    the feeding plate in its region arranged proximally to the contact point of the pushing device has a middle section standing out upwards which is positioned close to the clips guided in the magazine.

2. Placing instrument according to claim 1 wherein the pushing device is a bar that is arranged under the feeding plate and that can be pushed forwards and pulled backwards, said bar having a side projection which when said bar is pushed forwards, comes into contact with an edge of the feeding plate standing out downwards out of the plane of the feeding plate.

3. Placing instrument according to claim 2 wherein the edge is formed by the middle section of the feeding plate, said middle section standing out downwards.

4. Placing instrument according to claim 3 wherein the feeding plate runs parallel to the guiding groove of the magazine and can be pushed in said longitudinal direction in the magazine.

5. Placing instrument according to claim 3 wherein the bar is arranged proximally to the side projection close to the middle section of the feeding plate standing out downwards, an has recesses that form receptive chambers for the flexible lugs of the feeding plate when the bar is pulled back.

6. Placing instrument according to claim 2 wherein the bar is arranged proximally to the side projection close to the middle section of the feeding plate, standing out downwards and has recesses that form receptive chambers for the flexible lugs of the feeding plate when the bar is pulled back.

7. Placing instrument according to claim 4 wherein the bar has a circular cross section and wherein the side projection and the recesses are formed by ring collars or ring grooves respectively.

8. Placing instrument according to claim 4 wherein the bar has a circular cross section and wherein the side projection and the recesses are formed by ring collars and ring grooves respectively.

9. Placing instrument according to claim 6 wherein the pushing device, when pulled back, contacts a flexible lug of the feeding plate with a side projection.

10. Placing instrument according to claim 6 wherein the feeding plate runs parallel to the guiding groove of the magazine and can be pushed in said longitudinal direction in the magazine.

11. Placing instrument according to claim 2 wherein the feeding plate runs parallel to the guiding groove of the magazine and can be pushed in said longitudinal direction in the magazine.

12. Placing instrument according to claim 1 wherein the pushing device, when pulled back, contacts a flexible lug of the feeding plate with a side projection.

13. Placing instrument according to claim 12 wherein the flexible lug is arranged at the proximal end of the feeding plate.

14. Placing instrument according to claim 12 wherein side projections on the pushing device are at a shorter distance to one another than corresponding contact points on the feeding plate.

15. Placing instrument according to claim 12 wherein the feeding plate runs parallel to the guiding groove of the magazine and can be pushed in said longitudinal direction in the magazine.

16. Placing instrument according to claim 1 wherein the feeding plate runs parallel to the guiding groove of the magazine and can be pushed in said longitudinal direction in the magazine.

17. Placing instrument according to claim 1 wherein the clips are held in a detachable frictional connection in the guiding groove of the magazine.

* * * * *

UNITED STATES PATENT AND TRADEMARK OFFICE
CERTIFICATE OF CORRECTION

PATENT NO. : 6,837,895 B2
DATED : January 4, 2005
INVENTOR(S) : Mayenberger

It is certified that error appears in the above-identified patent and that said Letters Patent is hereby corrected as shown below:

Column 7,
Line 55, delete the word "the" at the beginning of the line.

Column 8,
Line 19, after the word "plate" insert a -- , --.
Line 20, change the word "an" to -- and --.

Signed and Sealed this

Fifth Day of April, 2005

JON W. DUDAS
*Director of the United States Patent and Trademark Office*